United States Patent
Asaka et al.

[11] Patent Number: 6,140,479
[45] Date of Patent: Oct. 31, 2000

[54] ERYTHROMYCIN A DERIVATIVES

[75] Inventors: Toshifumi Asaka; Takaaki Ishii; Tetsuya Tanikawa; Masato Kashimura, all of Tokyo, Japan

[73] Assignee: Taisho Pharmaceuticals Co., Ltd., Japan

[21] Appl. No.: 09/381,507

[22] PCT Filed: Mar. 23, 1998

[86] PCT No.: PCT/JP98/01240
§ 371 Date: Sep. 21, 1999
§ 102(e) Date: Sep. 21, 1999

[87] PCT Pub. No.: WO98/42720
PCT Pub. Date: Oct. 1, 1998

[30] Foreign Application Priority Data

Mar. 24, 1997 [JP] Japan ............................. 9-69329

[51] Int. Cl.[7] ................... C07H 17/08; A61K 31/70
[52] U.S. Cl. ................ 536/7.2; 536/7.4; 514/29; 574/29
[58] Field of Search ............ 536/7.2, 7.4; 514/29; 574/29; A61K 31/70; C07H 17/08

[56] References Cited

U.S. PATENT DOCUMENTS

| | | | |
|---|---|---|---|
| 3,923,784 | 12/1975 | Kierstead et al. | 560/210 |
| 4,331,803 | 5/1982 | Watanabe et al. | 536/7.2 |
| 4,742,049 | 5/1988 | Baker et al. | 514/29 |
| 5,631,354 | 5/1997 | Asaka et al. | 536/7.4 |
| 5,656,607 | 8/1997 | Agouridas et al. | 514/29 |
| 5,770,579 | 6/1998 | Agouridas et al. | 514/29 |

FOREIGN PATENT DOCUMENTS

| | | |
|---|---|---|
| 487411 | 11/1991 | European Pat. Off. |
| 619320 | 12/1992 | European Pat. Off. |
| 638584 | 4/1993 | European Pat. Off. |
| 676409 | 4/1995 | European Pat. Off. |
| 62-292795 | 12/1987 | Japan |
| 7278177 | 10/1995 | Japan |

*Primary Examiner*—Nita Minnifield
*Assistant Examiner*—Padma Baskar
*Attorney, Agent, or Firm*—Lorusso & Loud

[57] ABSTRACT

An erythromycin A derivative represented by Formula (I):

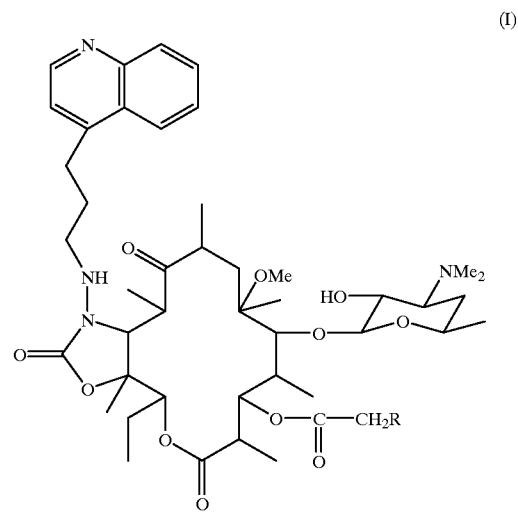

(I)

wherein R is a pyridyl group, a quinolyl group, a nitrophenyl group or a methoxyphenyl group, or a pharmaceutically acceptable salt thereof has a strong antibacterial activity not only against erythromycin-sensitive bacteria but also against certain erythromycin-resistant bacteria and Haemophilus influenzae.

2 Claims, No Drawings

ERYTHROMYCIN A DERIVATIVES

TECHNICAL FIELD

The present invention relates to antibiotic erythromycin A derivatives.

BACKGROUND ART

Erythromycin A is an antibiotic widely used as an agent for treating infectious diseases caused by Gram-positive bacteria, mycoplasmas, etc. However, erythromycin is decomposed by gastric acid due to its instability to acids, and thus has a drawback of no constancy of movement in the body. Hitherto many erythromycin derivatives have been prepared for the purpose of the improvement of such biological or pharmacological properties. For example, it is reported that 6-O-methylerythromycin A derivatives have an improved stability to acids and have a superior in vivo antibacterial activity in comparison with erythromycin A when administered orally (U.S. Pat. No. 433,803). There are also recent reports relating to 11,12-cyclic carbamate derivatives of erythromycin with the aim of expansion of antibacterial spectrum as well as a stability to acids (EP. patent No. 487411, U.S. Pat. No. 4742049, EP. patent No. 676409 and EP. patent No. 638584), and further reports relating to erythromycin derivatives wherein an acyl group has been introduced at the 3-position (EP. Patent No. 619320).

An object of the present invention is to provide novel antibiotics having a strong antibacterial activity not only against previous erythromycin-sensitive bacteria but also against *Haemophilus influenzae* and erythromycin-resistant bacteria which recently show a tendency to increase.

DISCLOSURE OF THE INVENTION

As a result of various researches on the antibacterial activity of erythromycin derivatives, the present inventors have found that, among the 11,12-cyclic carbamate derivatives of 6-O-methylerythromycin A, the compounds containing a certain type of acyl group introduced at the 3-position have a strong antibacterial activity not only against previous erythromycin-sensitive bacteria but also against *Haemophilus influenzae* and certain erythromycin-resistant bacteria, thereby the present invention has been accomplished.

The present invention relates to an erythromycin derivative represented by Formula (I):

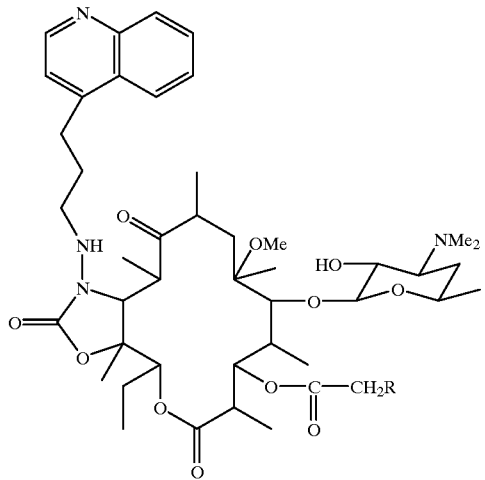

wherein R is a pyridyl group, a quinolyl group, a nitrophenyl group or a methoxyphenyl group; or a pharmaceutically acceptable salt thereof.

In the present invention, the pharmaceutically acceptable salt refers to a salt used in chemotherapy or prophylaxis of bacterially infectious diseases. It includes, for example, a salt with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanic acid, polyacrylate and carboxyvinyl polymer.

The compounds of the present invention can be prepared, for example, as follows.

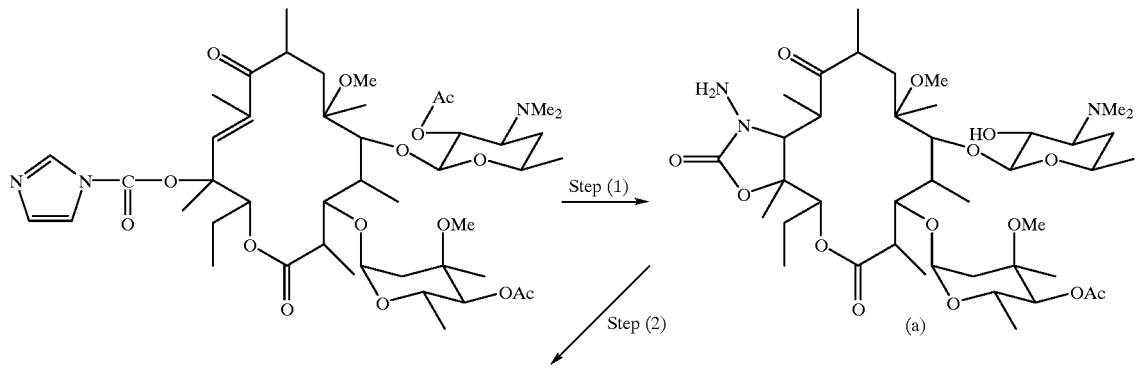

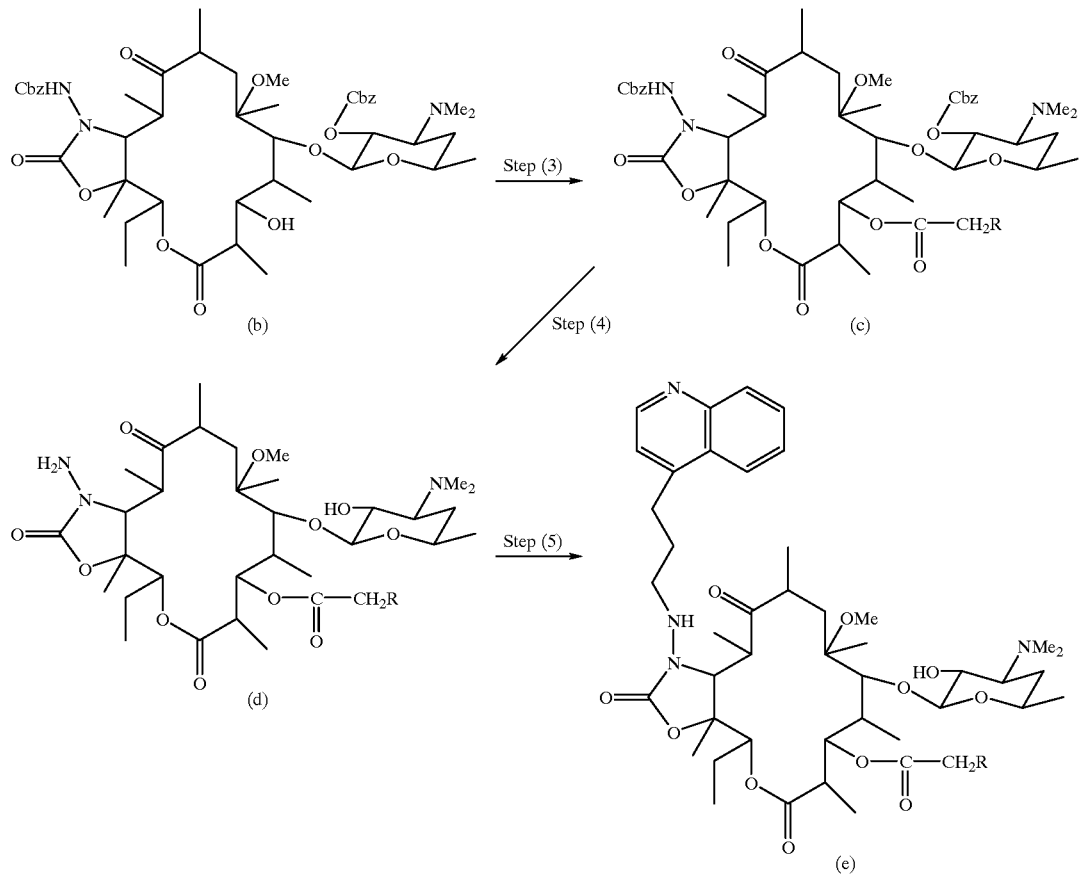

Step (1); 10,11-Anhydro-2',4"-di-O-acetyl-12--imidazolylcarbonyl-6-O-methylerythromycin A described in EP patent No. 638584 is reacted with hydrazine or ydrazine monohydrate in an inert solvent at a temperature of from $-30$ to $100°$ C., preferably from $0°$ C. to room temperature, to give an 11,12-cyclic carbamate compound, which is then reacted in a lower alcohol or an aqueous lower alcohol (if desired, a base such as sodium bicarbonate may be added herein) at a temperature of from 0 to $100°$ C for removal of the protective group at the 2'-position, thereby there is obtained a compound represented by Formula (a). Examples of the inert solvent to be used herein are acetonitrile, tetrahydrofuran, N,N-dimethylformamide, dioxane, ethyl acetate, N-methylpyrrolidone, an aqueous solvent thereof and a mixture thereof. Examples of the lower alcohol used herein are methanol, ethanol and propyl alcohol.

Step (2); To Compound (a) is added benzyl chloroformate in an inert solvent in the presence of sodium bicarbonate under ice-cooling, followed by reacting them at a temperature of from 0 to $100°$ C., preferably from room temperature to $60°$ C., to give a bis-benzyloxycarbonyl compound, which is then reacted with an acid such as hydrochloric acid (if desired, a mixture of a lower alcohol and the acid may be used herein) for removal of the sugar at the 3-position, thereby there is obtained a compound represented by Formula (b). The inert solvent and the lower alcohol to be used herein are the same as in Step (1).

Step (3); Compound (b) is reacted using a reagent represented by the formula:

R—CH$_2$COOH (wherein R is as defined above) and an activating agent thereof in an inert solvent in the presence of a base such as triethylamine or 4-dimethylaminopyridine at a temperature of $-30$ to $30°$ C. to give a compound represented by Formula (c). Examples of the activating agent to be used herein are 1,3-dicyclohexylcarbodiimide, 1-(3-dimethylaminopropyl)-3-ethylcarbodiimide hydrochloride and pivaloyl chloride, and examples of the inert solvent to be used herein are dichloromethane, dichloroethane, acetone, pyridine, ethyl acetate and tetrahydrofuran.

Step (4); Compound (c) is subjected to hydrogenolysis in an ordinary manner to give a compound represented by Formula (d) (wherein R is as defined above).

Step (5); Compound (d) is reacted in an inert solvent in the presence of an acid such as acetic acid using 3-(4-quinolyl)propanal and a reducing agent to give a compound of the present invention represented by Formula (e) (wherein R is as defined above). Examples of the inert solvent to be used herein are methanol, ethanol and dichloromethane, and examples of the reducing agent to be used herein are sodium borohydride, sodium cyanoborohydride and sodium triacetoxyborohydride.

The erythromycin A derivatives of the present invention can be administered orally or parenterally. It can be administered in a dosage form such as tablets, capsules, powders, troches, ointments, suspensions, suppositories or injectional preparations, all of which can be prepared by conventional preparation techniques. The dose is from 50 to 1,000 mg per day for the treatment of adults, and it can be administered in 2 or 3 portions. This dose can be properly increased or decreased depending on the age, body weight and conditions of the patient.

MODE FOR CARRYING OUT THE INVENTION

The present invention is illustrated in more detail by the following examples and experiment.

EXAMPLE 1

Preparation of 11-deoxy-11-{2-(3-(4-quinolyl)propyl) hydrazino}-3-O-(3-pyridyl)acetyl-5-O-desosaminyl-6-O-methylerythronolide A 11,12-cyclic carbamate (1) In 50 ml of acetonitrile was dissolved 5.45 g (6.0 mmol) of 10, 11-anhydro-2',4"-di-O-acetyl-12-O-imidazolylcarbonyl-6-O-methylerythromycin A described in EP patent No. 638584, and then 1.50 ml (30.0 mmol) of hydrazine monohydrate was added thereto at room temperature, followed by stirring overnight. The reaction solution was evaporated under reduced pressure, and the residue was dissolved in 50 ml of methanol and refluxed under heating for 4 hours. After evaporation of the solvent, the residue was dissolved in 60 ml of tetrahydrofuran, and then 3.0 g (36.0 mmol) of sodium bicarbonate and 2.6 ml (18 mmol) of benzyl chloroformate were added thereto, followed by stirring under ice-cooling. The reaction temperature was raised to 50° C., followed by stirring overnight. The reaction solution was made basic by addition of 4N sodium hydroxide and extracted with chloroform. The organic layer was dried over anhydrous magnesium sulfate, and the solvent was evaporated under reduced pressure. The residue was dissolved in ethanol, and after addition of 2N hydrochloric acid, stirred at 60° C. for 8 hours. After the reaction, the reaction solution was made basic by addition of 4N aqueous sodium hydroxide solution, and extracted with chloroform. The organic layer was dried over anhydrous magnesium sulfate, and the solvent was evaporated under reduced pressure. The residue was purified by silica gel column chromatography (hexane acetone:triethylamine=10:3:0.3) to give 3.4 g of 2'-O-benzyloxycarbonyl-11-(2-(N-benzyloxycarbonyl)hydrazino)-5-O-desosaminyl-6-O-methylerythronolide A 11,12-cyclic carbamate.

(2) In 15 ml of dichloromethane were dissolved 1.74 g (10.0 mmol) of 3-pyridylacetic acid hydrochloride, 1.86 ml (13.3 mmol) of triethylamine and 1.24 ml (10.1 mmol) of pivaloyl chloride, followed by stirring at −15° C. for 20 minutes. To the solution was added a solution of 3 g (3.34 mmol) of the compound obtained in the above (1) in 15 ml of dichloromethane, and after stirring for 10 minutes, 409 mg (3.35 mmol) of 4-dimethylaminopyridine was added thereto, and then stirring was further continued for 1.5 hours. The reaction solution was concentrated under reduced pressure and extracted with ethyl acetate. The organic layer was washed with water and a saturated aqueous sodium chloride solution successively, and dried over anhydrous magnesium sulfate, and the solvent was evaporated under reduced pressure. The residue was purified by silica gel column chromatography (hexane:acetone:triethylamine=10:6:0.2) to give 2.59 g of the 3-O-pyridylacetyl compound.

(3) In 15 ml of methanol was dissolved 2.3 g (2.26 mmol) of the compound obtained in the above (2), and then 0.46 g of 10% palladium carbon and 1.43 g (22.7 mmol) of ammonium formate were added thereto, followed by stirring at room temperature for 4 hours. After removal of the catalyst by filtration, the filtrate was concentrated under reduced pressure and worked up in the same manner as in the above (2) using chloroform as an extract solvent. After evaporation of the solvent, the residue was purified by silica gel column chromatography (chloroform:methanol:aqueous ammonia=20:1:0.1) to give 1.39 g of the 11-hydrazino-11,12-cyclic carbamate compound.

(4) In 10 ml of methanol was dissolved 0.10 g (0.13 mmol) of the compound obtained in the above (3), and then 53 mg (0.26 mmol) of 3-(4-quinolyl)propanal (of which preparation method was shown in Reference Example 1) and 61 µl (1.1 mmol) of acetic acid were added thereto. Thereafter, 33.4 mg (0.53 mmol) of sodium cyanoborohydride was added to the resulting solution under ice-cooling, the temperature thereof was returned to room temperature, followed by stirring overnight. The reaction solution was made basic by addition of 4N sodium hydroxide and extracted with diethyl ether. The organic layer was dried over anhydrous magnesium sulfate, and the solvent was evaporated under reduced pressure. The residue was purified by silica gel column chromatography (chloroform:methanol:aqueous ammonia=10:1:0.1) to give 0.10 g of the title compound.

REFERENCE EXAMPLE 1

Preparation of 3-(4-quinolyl)propanal to be used in Example 1 (4)

(1) In 100 ml of methanol was dissolved 7.92 g (50.4 mmol) of 4-quinolinecarboxaldehyde, and then 8.9 ml (55.4 mmol) of trimethylphosphonoacetate $(MeO)_2P(O)CH_2CO_2Me$ and 13.9 g (101 mmol) of potassium carbonate were added thereto, followed by stirring at room temperature for 2 hours. The reaction solution was diluted with diethyl ether and then washed with water. The organic layer was dried over anhydrous magnesium sulfate, and the solvent was evaporated under reduced pressure. The residue was dissolved in 100 ml of methanol, and after addition of 4.0 g of 5% palladium carbon, stirred under a hydrogen gas stream for 2 hours. The palladium carbon was filtered through Celite, and the solvent was evaporated under reduced pressure to give 10.7 g of the ester compound. (2) In 250 ml of anhydrous diethyl ether was dissolved 10.7 g (49.7 mmol) of the ester compound obtained in the above (1), and then 3.77 g (99.4 mmol) of lithium aluminum hydride was added thereto under ice-cooling, followed by stirring for an hour. 3.8 Milliliters of water and 3.8 ml of 4N sodium hydroxide then an additional 11.6 ml of water were added to the solution, followed by stirring for an hour. The precipitate was removed by filtration, and the solvent was evaporated under reduced pressure to give 6.9 g of the alcohol compound.

(3) In 5.0 ml of dichloromethane was dissolved 0.43 ml (6.0 mmol) of dimethyl sulfoxide, followed by stirring at −60° C. To the resulting solution was dropwise added a solution of 0.26 ml (3.0 mmol) of oxalyl chloride in 5 ml of dichloromethane and stirred for 10 minutes. To the solution was then added dropwise a solution of 0.30 g (1.50 mmol) of the alcohol compound obtained in the above (2) in 5.0 ml of dichloromethane. 1.66 Milliliters (12.0 mmol) of triethylamine was added thereto, followed by stirring for 10 minutes. After the reaction, the reaction solution was washed with distilled water and then with an aqueous sodium chloride solution. The organic layer was dried over anhydrous magnesium sulfate, and the solvent was evaporated under reduced pressure to give 0.30 g of 3-(4-quinolyl) propanal. Experiment [In Vitro Antibacterial Activity]

The in vitro antibacterial activity of the compound obtained in Example 1 as an example of the compound of the present invention against various experimental bacteria was measured using sensitive disc media (produced by Eiken Chemical Co.) according to the MIC measuring method specified by the Japan Society of Chemotherapy. Erythromycin A was used as a comparative drug. The results are expressed as MIC value (Minimum Inhibitory Concentration against microorganism, µg/ml), and shown in Table 1. The compound obtained in Example 1 was indicated to have a strong antibacterial activity not only against erythromycin-sensitive bacteria but also against *Haemophilus influenzae* and certain erythromycin- resistant bacteria.

TABLE 1

| Microorganism/Compound | Comparative drug | Compound of Example 1 |
|---|---|---|
| *S. aureus* 209P-JC | 0.20 | 0.10 |
| *S. aureus* B1 | >100 | 0.10 |
| *S. pneumoniae* IID553 | 0.10 | 0.20 |
| *S. pneumoniae* BM210 | 0.78 | 0.20 |
| *S. pneumoniae* BM205 | >100 | 0.39 |
| *H. influenzae* ATCC 19418 | 6.25 | 3.13 |

Industrial Applicability

The compounds of the present invention have a strong antibacterial activity not only against erythromycin-sensitive bacteria but also against certain erythromycin-resistant bacteria and *Haemophilus influenzae*. Accordingly, the compounds of the present invention are useful as antibacterial agents for the treatment of bacterially infectious diseases in human beings and animals (including farm animals).

What is claimed is:

1. An erythromycin A derivative represented by Formula (I):

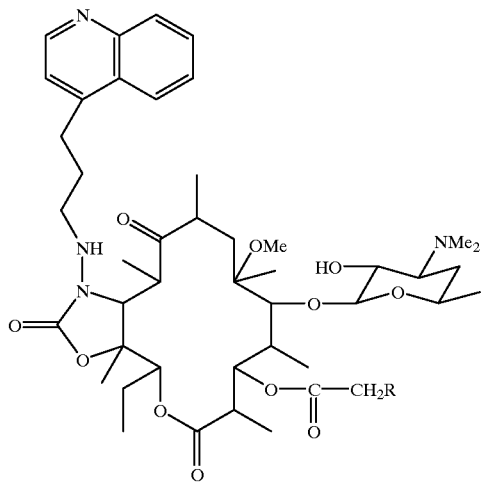

wherein R is a pyridyl group, a quinolyl group, a nitrophenyl group or a methoxyphenyl group; or a pharmaceutically acceptable salt thereof.

2. A method for the treatment of an infectious bacterial disease which comprises administering the erythromycin A compound or the pharmaceutically acceptable salt thereof according to claim 1 to a patient in an amount effective for said treatment.

* * * * *

UNITED STATES PATENT AND TRADEMARK OFFICE
CERTIFICATE OF CORRECTION

PATENT NO. : 6,140,479
DATED : October 31, 2000
INVENTOR(S) : Asaka et al.

It is certified that error appears in the above-identified patent and that said Letters Patent is hereby corrected as shown below:

Title page,
Item [73], "Assignee: Taisho Pharmaceuticals Co., Ltd.," should read -- Assignee: Taisho Pharmaceutical Co., Ltd. --.

Column 1,
Line 21, "433,803" should read -- 4,331,803 --.

Column 3,
Line 38, "12- -" should read -- 12-0- --; and
Line 40, "ydrazine" should read -- hydrazine --.

Column 6,
Line 35, begin a new paragraph with "(2)".

Signed and Sealed this

Twenty-fifth Day of December, 2001

JAMES E. ROGAN
*Director of the United States Patent and Trademark Office*

*Attest:*

*Attesting Officer*